(12) United States Patent
Kent

(10) Patent No.: US 12,083,341 B2
(45) Date of Patent: Sep. 10, 2024

(54) SYSTEMS AND METHODS FOR TREATING SLEEP DISORDERED BREATHING

(71) Applicant: Vanderbilt University, Nashville, TN (US)

(72) Inventor: David Kent, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 131 days.

(21) Appl. No.: 17/278,807

(22) PCT Filed: Mar. 6, 2020

(86) PCT No.: PCT/US2020/021359
§ 371 (c)(1),
(2) Date: Mar. 23, 2021

(87) PCT Pub. No.: WO2020/185549
PCT Pub. Date: Sep. 17, 2020

(65) Prior Publication Data
US 2022/0032052 A1    Feb. 3, 2022

Related U.S. Application Data

(60) Provisional application No. 62/843,641, filed on May 6, 2019, provisional application No. 62/815,393, filed on Mar. 8, 2019.

(51) Int. Cl.
*A61N 1/36* (2006.01)
*A61N 1/05* (2006.01)

(52) U.S. Cl.
CPC .......... *A61N 1/3611* (2013.01); *A61N 1/0551* (2013.01); *A61N 1/36139* (2013.01)

(58) Field of Classification Search
None
See application file for complete search history.

(56) References Cited

U.S. PATENT DOCUMENTS

| | | | |
|---|---|---|---|
| 5,591,216 A * | 1/1997 | Testerman | A61N 1/3601 607/42 |
| 7,367,935 B2 | 5/2008 | Mechlenburg et al. | |
| 8,965,535 B2 | 2/2015 | Dunlay | |
| 10,213,600 B2 | 2/2019 | Tyler | |
| 2001/0018547 A1 | 8/2001 | Mechlenburg | |
| 2003/0153953 A1 | 8/2003 | Park et al. | |
| 2009/0014012 A1 * | 1/2009 | Sanders | A61N 1/3601 128/848 |
| 2012/0022626 A1 | 1/2012 | Bolea | |
| 2012/0234331 A1 * | 9/2012 | Shantha | A61F 5/566 128/848 |
| 2013/0253627 A1 | 9/2013 | Meadows et al. | |

OTHER PUBLICATIONS

International Search Report and Written Opinion mailed Jun. 3, 2020 for corresponding International Application No. PCT/US2020/021359.

* cited by examiner

*Primary Examiner* — Ankit D Tejani
(74) *Attorney, Agent, or Firm* — Tarolli, Sundheim, Covell & Tummino LLP

(57) ABSTRACT

Methods and systems of treating sleep disordered breathing in a patient suffering therefrom by activating one or more infrahyoid strap muscles are provided. Activation of one or more infrahyoid muscles can be accomplished by stimulating an ansa cervicalis, including one or both of the superior root and the inferior root of the ansa cervicalis, alone or in combination with stimulating the hypoglossal nerve.

20 Claims, 5 Drawing Sheets

SYSTEMS AND METHODS FOR TREATING SLEEP DISORDERED BREATHING

CROSS-REFERENCE TO RELATED APPLICATIONS

The present application is a U.S. National Stage application under 35 USC 371 of PCT Application Serial No. PCT/US2020/021359, filed Mar. 6, 2020; which claims priority to U.S. Provisional Application No. 62/843,641 filed on May 6, 2019 and U.S. Provisional Application No. 62/815,393 filed on Mar. 8, 2019, both of which are incorporated by reference herein.

TECHNICAL FIELD

The present disclosure relates to methods and systems for treating sleep disordered breathing by activating infrahyoid strap muscles via neuromodulation.

BACKGROUND

Sleep disordered breathing (SDB) occurs when there is a partial or complete cessation of breathing that occurs many times throughout the night. Obstructive sleep apnea (OSA) is a type of SDB that involves cessation or significant decrease in airflow in the presence of breathing effort. It is the most common type of SDB and is characterized by recurrent episodes of upper airway collapse during sleep inducing repetitive pauses in breathing followed by reductions in blood oxygen saturation or neurologic arousal. The pathophysiology of OSA can involve factors such as craniofacial anatomy, airway collapsibility, and neuromuscular control of the upper airway dilator musculature. Electromyogram studies have shown that the tonic and phasic activity of the pharyngeal airway dilatory muscles (such as the genioglossus muscle) is progressively reduced from wakefulness to non-rapid eye movement to rapid eye movement.

Continuous positive airway pressure (CPAP) therapy is the frontline treatment for OSA. CPAP therapy utilizes machines, generally including a flow generator, tubing, and a mask designed to deliver a constant flow of air pressure to keep the airways continuously open in patients with OSA. However, the success of CPAP therapy is limited by compliance with reported rates ranging from 50% to 70%. Hypoglossal nerve stimulation (HNS) has now been established as an effective form of therapy for patients with obstructive sleep apnea (OSA) who are unable to tolerate positive airway pressure. This therapy works by protruding and stiffening the tongue muscle thereby dilating the pharyngeal airway. However, only a small subset of patients with OSA have anatomy suitable for hypoglossal nerve stimulation therapy, as many patients continue to suffer from airway collapse even with stimulation of hypoglossal nerve musculature.

SUMMARY

The present disclosure relates to methods and systems for treating SDB in a patient suffering therefrom by activating infrahyoid strap muscles via neuromodulation. In an aspect, a method for improving SDB in a patient suffering therefrom comprises delivering a neuromodulation signal to a target site proximate to an ansa cervicalis that innervates a sternothyroid muscle and activating the sternothyroid muscle to improve the patient's SDB. In another aspect, a method for improving SDB in a patient suffering therefrom comprises delivering a neuromodulation signal to a target site proximate to an ansa cervicalis that innervates a sternothyroid muscle to activate the sternothyroid muscle. The method further involves delivering a neuromodulation signal to a target site proximate to a hypoglossal nerve (HGN) to activate a genioglossus muscle. Delivery of the neuromodulation signals can improve the patient's SDB. Aspect of the present disclosure can further include delivering a neuromodulation signal to a target site proximate to an ansa cervicalis that innervates a sternohyoid muscle to activate the sternohyoid muscle to improve the patient's SDB.

DETAILED DESCRIPTION

The present disclosure relates to systems and methods for improving SDB by activating one or more infrahyoid strap muscles. Non-limiting examples of SDBs are increased upper airway resistance including snoring; upper airway resistance syndrome (UARS); and sleep apnea. Sleep apnea can include OSA, central sleep apnea (CSA), and mixed sleep apnea. As used herein with respect to a described element, the terms "a," "an," and "the" include at least one or more of the described element unless otherwise indicated. Further, the terms "or" and "and" refer to "and/or" and combinations thereof unless otherwise indicated. Reference to "improving" a patient's SDB includes treating, reducing the symptoms of, mitigating, or preventing the SDB. In certain aspects, a method of improving a patient's SDB is preventative as opposed to reactionary in nature. In other words, a method of improving a patient's SDB according to certain aspects involves preventing SDB as opposed to detecting an apnea or hypopnea event, for example, and responding to such detected event. By preventing SDB, a treatment method can reduce the potential for airway collapse as opposed to reacting to a documented event. As used herein, "neuromodulation," "neuromodulate," "neurostimulation," "neurostimulate," "stimulation," or "stimulate" refers to exciting or inhibiting neural activity. A patient suffering from SDB includes a mammal, such as a human being.

The present disclosure provides methods and systems for treating SDB in a patient suffering therefrom by activating one or more infrahyoid strap muscles. Activation of one or more infrahyoid muscles can be accomplished by stimulating an ansa cervicalis, including one or both of the superior root and the inferior root of the ansa cervicalis, alone or in combination with stimulating the HGN. The stimulation can be electrical stimulation. Further, stimulation includes unilateral stimulation as well as bilateral stimulation of these nerve(s). Without wishing to be bound by a particular mechanism of action, it is believed that activation of infrahyoid muscles (e.g. tightening of these muscles) can reduce upper airway compliance (e.g. stiffen the upper airway). Upper airway compliance can indicate the potential of the airway to collapse and can be relevant to treating SDB. As explained below, the infrahyoid muscles include the sternohyoid muscle, the sternothyroid muscle, the omohyoid muscle, and the thyrohyoid muscle. In an aspect, the present disclosure provides a method of activating one or more of these muscles either alone or in combination with activating the genioglossus muscle. Activation of the genioglossus muscle can be accomplished by neuromodulating the hypoglossal nerve (HGN).

Figure 1:
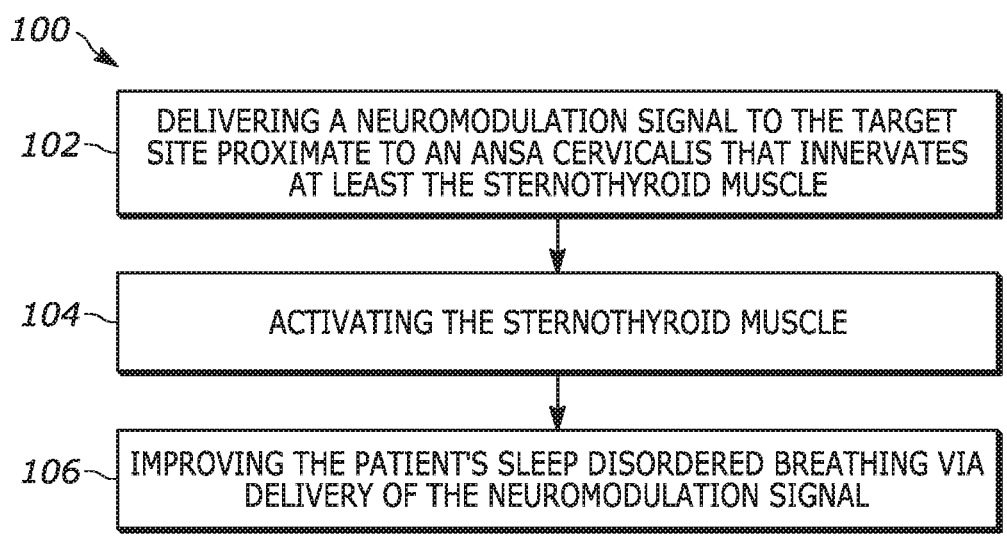
FIG. 1 is a flow chart depicting illustrative steps of a method of improving SDB in a patient suffering therefrom.

Referring to FIG. 1, in an aspect, a method (100) of treating SDB in a patient suffering therefrom comprises delivering a neuromodulation signal to a target site proximate to an ansa cervicalis that innervates at least the sternothyroid muscle (102). A target site can be proximate to the ansa cervicalis such that delivering a neuromodulation signal activates the motor fibers of the ansa cervicalis. Method 100 further includes activating the sternothyroid muscle (104). Method (100) further comprises improving the patient's SBD via delivery of the neuromodulation signal (106).

Figure 2:
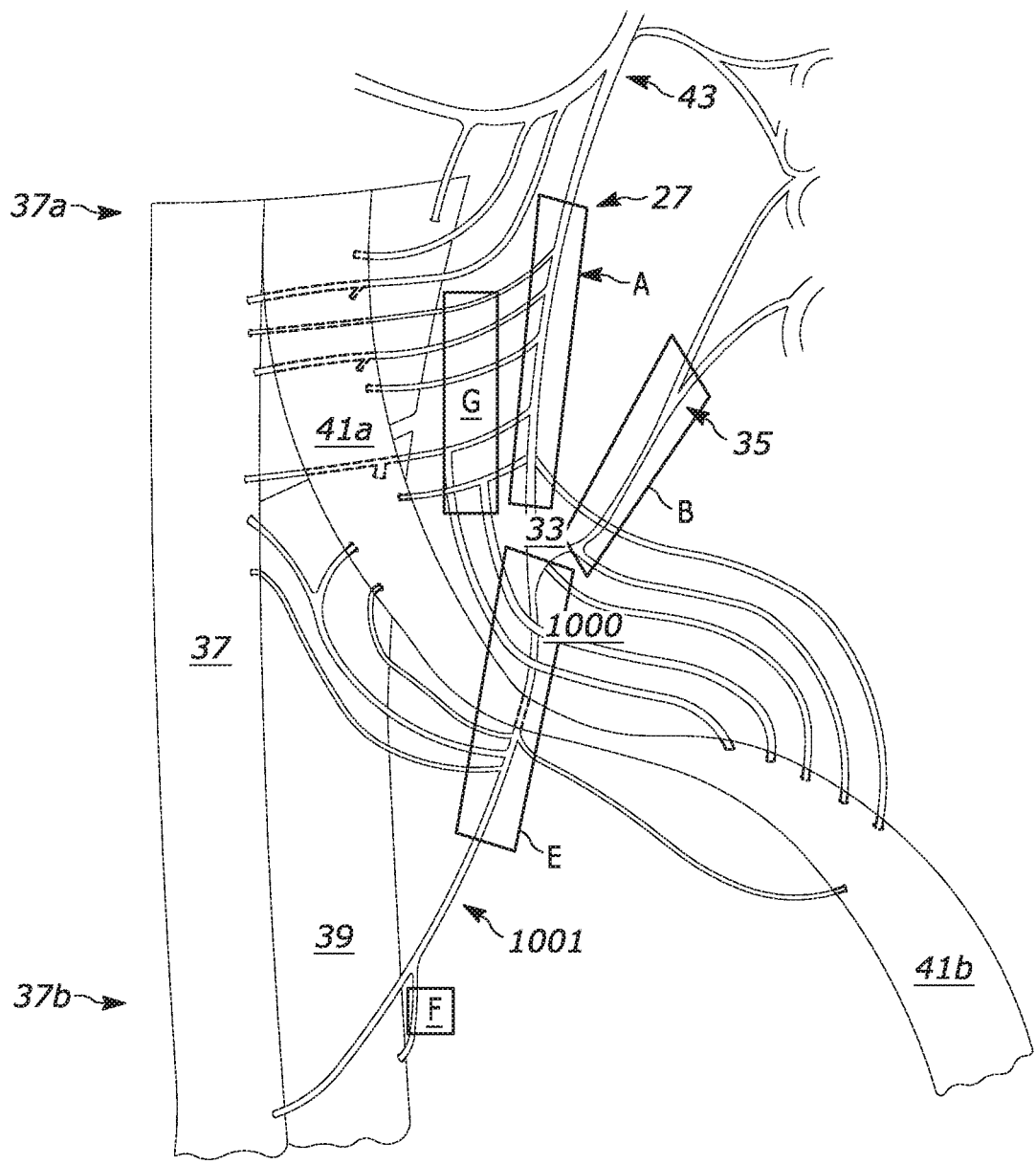
FIG. 2 is a schematic illustration of exemplary target sites for neuromodulation according to an aspect of the present disclosure.
Figure 3:
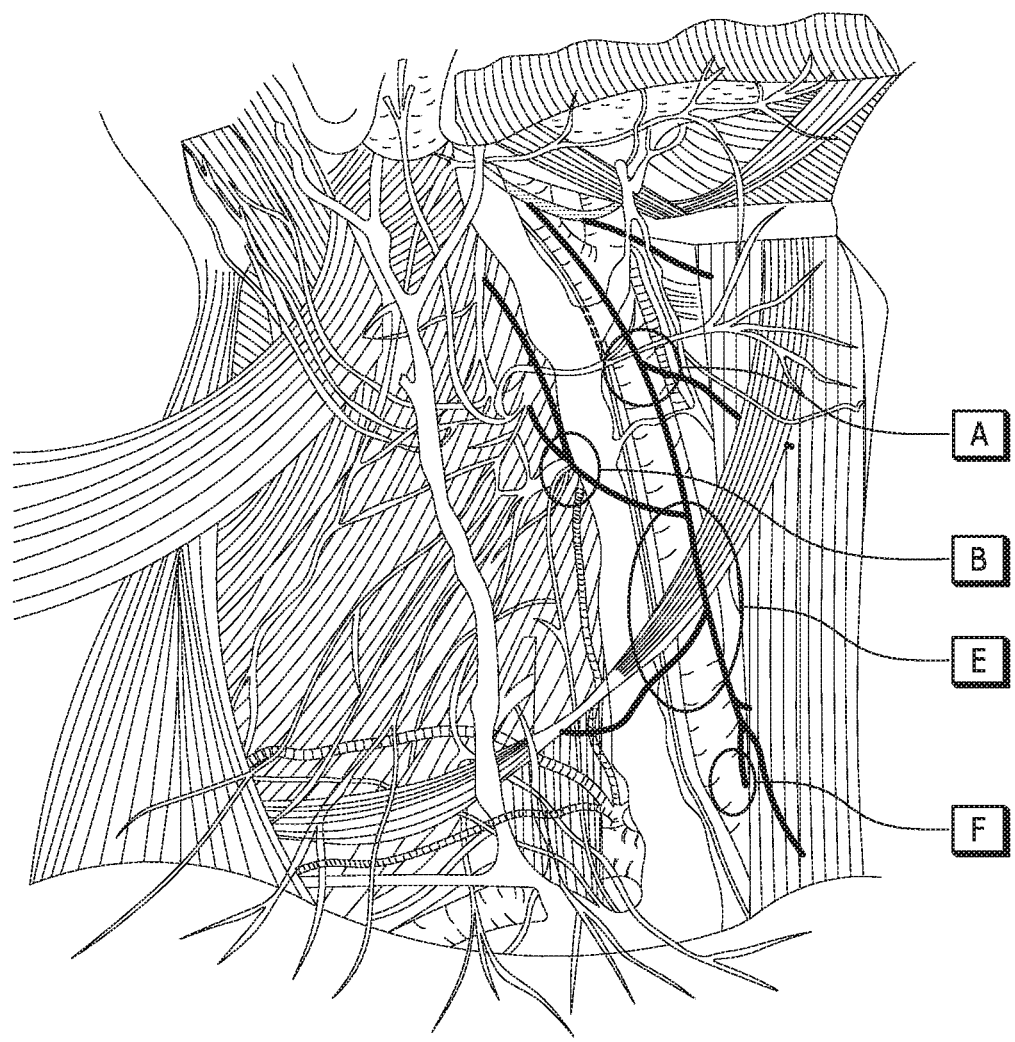
FIG. 3 is a schematic illustration of exemplary target sites for neuromodulation according to an aspect of the present disclosure.

With reference to FIGS. 2-3 the infrahyoid strap muscles can be variably innervated by nerve fiber contributions from both the superior and inferior roots of the ansa cervicalis. It should be noted that FIG. 2 generally illustrates most if not all known branching patterns of the ansa cervicalis but that no actual anatomic variant with all of these branching patterns would likely exist in a single patient. Normal anatomic variants may necessitate use of one or more different target sites in different patients to achieve desired stimulation of the sternothyroid muscle 39. In certain aspects and with reference to FIG. 2, a neuromodulation signal is delivered to a target site proximate to the ansa cervicalis 33 that also innervates the superior belly of the sternohyoid muscle 37a and/or inferior belly of the sternohyoid muscle 37b to activate part of or all of the sternohyoid muscle 37. For example, an exemplary target site includes target site A, which can be proximal to or at the branch point 43 of the superior root of the ansa cervicalis 27 innervating the sternohyoid muscle 37 such that the sternohyoid muscle 37 is activated as well as the sternothyroid muscle 39. In certain aspects, delivering a neuromodulation signal to target site A proximate to the superior root of the ansa cervicalis 27 can also activate part or all of the omohyoid muscle 41(a and b). If the target site were distal to the superior root of the ansa cervicalis 27 but not including branch point 1000 (e.g. placed in site G), a neuromodulation signal may only activate the sternohyoid muscle 37 and/or omohyoid muscle 41 and not necessarily the sternothyroid muscle 39 along with the sternohyoid muscle 37 and/or omohyoid muscle 41. Without wishing to be bound by a particular mechanism of action, it is believed that activation of at least the sternothyroid muscle 39, including the sternothyroid muscle 39, the sternohyoid muscle 37, and the omohyoid muscle 41 can stiffen the patient's upper airway thereby improving the patient's SDB.

In certain aspects, a neuromodulation signal is delivered to target site B proximate the ansa cervicalis (e.g. proximate to the inferior root of the ansa cervicalis 35) also innervating the sternothyroid muscle 39 and sternohyoid muscle 37 and omohyoid muscle 41 to activate one or more of the innervated muscles. In certain aspects, a neuromodulation signal can be delivered simultaneously to target sites A and B proximate the ansa cervicalis 31 in order to stimulate nerve branches from both the superior root 27 and inferior root 35 of the ansa cervicalis innervating the sternothyroid muscle 39 as well as the sternohyoid muscle 37 and omohyoid muscle 41. In certain aspects, delivering a neuromodulation signal to target site E (e.g. proximate to or at the branch point of the common trunk nerve or nerves 1000 arising from the loop of the ansa cervicalis 33 combining nerve fibers from the superior root 27 and inferior root 35 and supplying at least the sternothyroid muscle 39 and variably the sternohyoid muscle 37 and omohyoid muscle 41) can activate at least the sternothyroid muscle 39 and in certain aspects, the sternohyoid muscle 37 and in certain aspects the omohyoid muscle 41. In certain aspects, delivering a neuromodulation signal to target site F (e.g. proximate to or at the branch point of the sternothyroid muscle nerve or nerves from the common trunk 1001) can activate the sternothyroid muscle 39. The branches to the sternothyroid muscle can be a single nerve fiber or several closely located nerve fibers traveling together. It should be noted that the above target sites are only exemplary and a therapy device, such as electrode or electrodes, can be placed at other parts of the ansa cervicalis including branches thereof. In certain aspects, a neuromodulation signal is not delivered to the HGN proximal to branch point 43 as it is believed that separate, therapy devices, such as electrodes, may be needed to potentially provide different strength or timing of stimulation to the ansa cervicalis and HGN. In other aspects, the HGN can be stimulated proximal or distal to the branch point of the retrusor muscle branches to the stylohyoid muscle and/or the hyoglossus muscle. Further, stimulation can be applied to any combination of the above described sites and branches. For example, for target site E, a therapy device, such as an electrode or electrodes, can be placed proximal or distal to the branch to the omohyoid muscle such that stimulation is capturing only the sternothyroid/sternohyoid fibers. As another example, for target site F, a cuff electrode or electrodes could surround a single or multiple fibers innervating the sternothyroid muscle.

Figure 4:
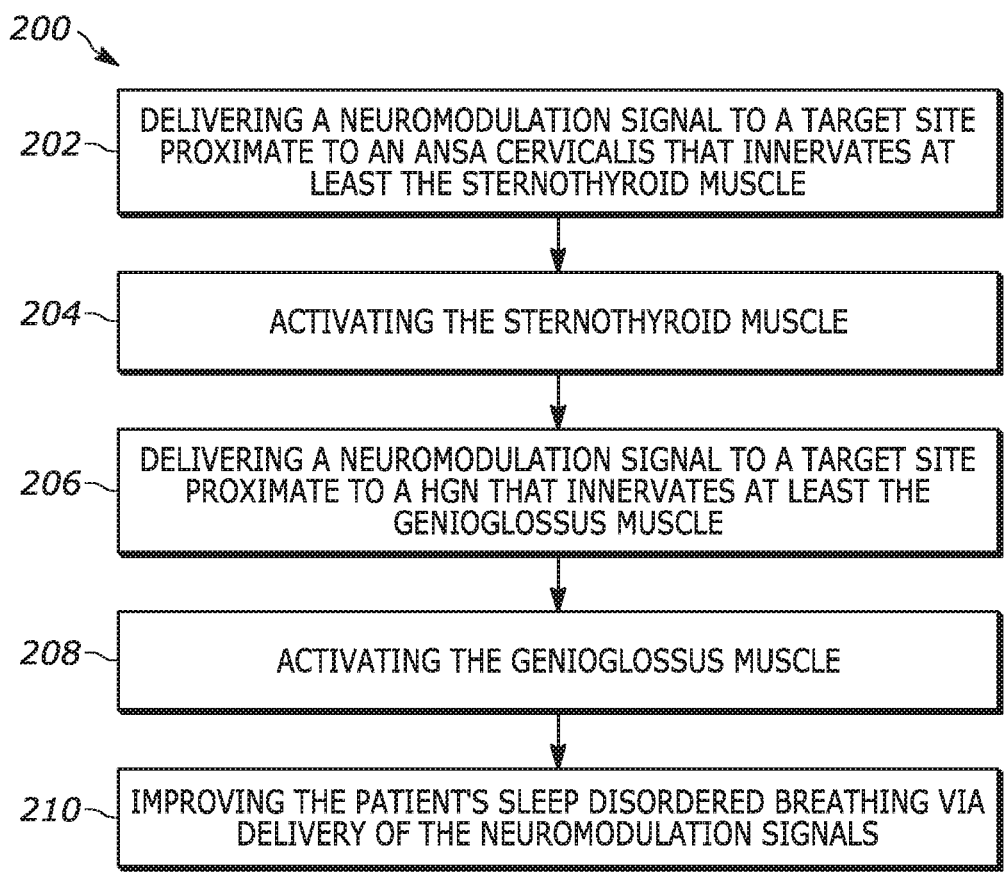
FIG. 4 is a flow chart depicting illustrative steps of a method of improving SDB in a patient suffering therefrom according to an aspect of the present disclosure.

Referring to FIG. 4, in another aspect, a method (200) for improving SDB in a patient suffering therefrom comprises delivering a neuromodulation signal to a target site proximate to an ansa cervicalis that innervates at least the sternothyroid muscle (202). Method 200 further includes activating the sternothyroid muscle (204). In certain aspects, a neuromodulation signal is delivered to a target site proximate to the ansa cervicalis that also innervates the sternohyoid muscle to activate the sternohyoid muscle as well. Method (200) further comprises delivering a neuromodulation signal to a target site proximate the HGN that innervate at least the genioglossus muscle (206). A target site can be proximate to the HGN such that delivering a neuromodulation signal activates the motor fibers of the HGN. Method (200) further includes activating the genioglossus muscle (208). Method (200) further comprises improving the patient's sleep disordered breathing via delivery of the neuromodulation signals (210). Without wishing to be bound by a particular mechanism of action, it is believed that activation of at least the sternothyroid muscle can stiffen the patient's upper airway and activation of at least the genioglossus muscle can cause the tongue to move forward and dilate/reinforce the patient's upper airway thereby improving a patient's SDB.

Delivering a neuromodulation signal, such as an electrical neuromodulation signal, can be accomplished by placing one or more therapy devices, such as electrodes/electrical contacts/neurostimulation devices, proximate to a target site innervating one or more infrahyoid strap muscles. The therapy device, such as the electrode, can be placed proximate to a target site in a variety of different ways, such as, for example, transcutaneously, percutaneously, subcutaneously, intramuscularly, intraluminally, transvascularly, intravascularly, or via direct open surgical implantation. The electrode can also have different form factors such as, for example, an injectable microstimulator, a nerve cuff electrode, or a transcutaneous patch.

An electrode or neurostimulator can be placed on the same or different target sites. For example, if the target sites include the superior root of the ansa cervicalis and the inferior root of the ansa cervicalis, a separate nerve cuff electrode can be placed on each root with each nerve cuff electrode having its own cathode and anode but connected to the same pulse generator or separate nerve cuff electrodes connected to the same pulse generator but one nerve cuff electrode serving as the cathode and the other serving as the anode, where the electrical field generated captures both roots. In certain embodiments, therapy device, such as an electrode or electrodes, configured to stimulate the ansa cervicalis can be combined with a therapy device, such as an electrode, configured to stimulate the hypoglossal nerve. Still alternatively, a therapy device, such as an electrode or electrodes, configured to stimulate the ansa cervicalis can be part of a device separate from a device configured to stimulate the hypoglossal nerve. The electrodes can be operably coupled to the same, single pulse generator or a separate pulse generator (either within the same physical housing or separate housings).

An electrode can be controllable to provide output signals that may be varied in voltage, frequency, pulse-width, current and intensity, for example. The electrode can also provide both positive and negative current flow from the electrode and/or can be capable of stopping current flow from the electrode and/or changing the direction of current flow from the electrode. An electrode can be in electrical communication with an electrical energy generator, such as a battery or pulse generator. For example, the electrical energy generator can include a battery that is rechargeable by inductive coupling. The electrical energy generator may be positioned in any suitable location, such as adjacent the electrode (e.g., implanted adjacent the electrode), or a remote site in or on the mammal's body or away from the mammal's body in a remote location. An electrode may be connected to the remotely positioned electrical energy generator wirelessly or via wires.

The electrical energy generator can control, for example, the pulse waveform, the signal pulse width, the signal pulse frequency, the signal pulse phase, the signal pulse polarity, the signal pulse amplitude, the signal pulse intensity, the signal pulse duration, and combinations thereof of an electrical neuromodulation signal. The electrical energy generator may be programmed to convey a variety of currents and voltages to one or more electrodes and thereby modulate the activity of a nerve, neuron, or nerve structure. The electrical energy generator may be programmed to control numerous electrodes independently or in various combinations as needed to provide neuromodulation. In some instances, an electrode may be powered by bringing a power source external to the patient's body into contact with the patient's skin, or which may include an integral power source.

An electrical neuromodulation signal may be constant, intermittent, varying and/or modulated with respect to the current, voltage, pulse-width, waveform, cycle, frequency, amplitude, and so forth. The waveform can be a sine wave, a square wave, or the like. The type of stimulation may vary and involve different waveforms. Optimal activation patterns may require a delay in one electrode before activating another or in another coordinated fashion to optimally open the airway, whether that involves simultaneous activation or staggered activation in a coordinated, adjustable fashion.

A controller or programmer may also be associated with the neurostimulation device. A programmer, for example, can include one or more microprocessors under the control of a suitable software program. The programmer can include other components such as an analog-to-digital converter, etc.

A neurostimulation device can be pre-programmed with desired stimulation parameters. Stimulation parameters can be controllable so that a neuromodulation signal may be remotely modulated to desired settings without removal of the electrode from its target position. Remote control may be performed, e.g., using conventional telemetry with an electric signal generator and battery, a radiofrequency receiver coupled to an external transmitter, and the like.

Methods as disclosed herein can be used as part of a closed-loop system (as described in more detail below). Such a method can include sensing a physiological parameter associated with SDB, generating a sensor signal based on the physiological parameter, and activating the therapy delivery device, such as an electrode, to adjust application of the neuromodulation signal to the target site in response to the sensor signal to improve the patient's SDB.

Figure 5:
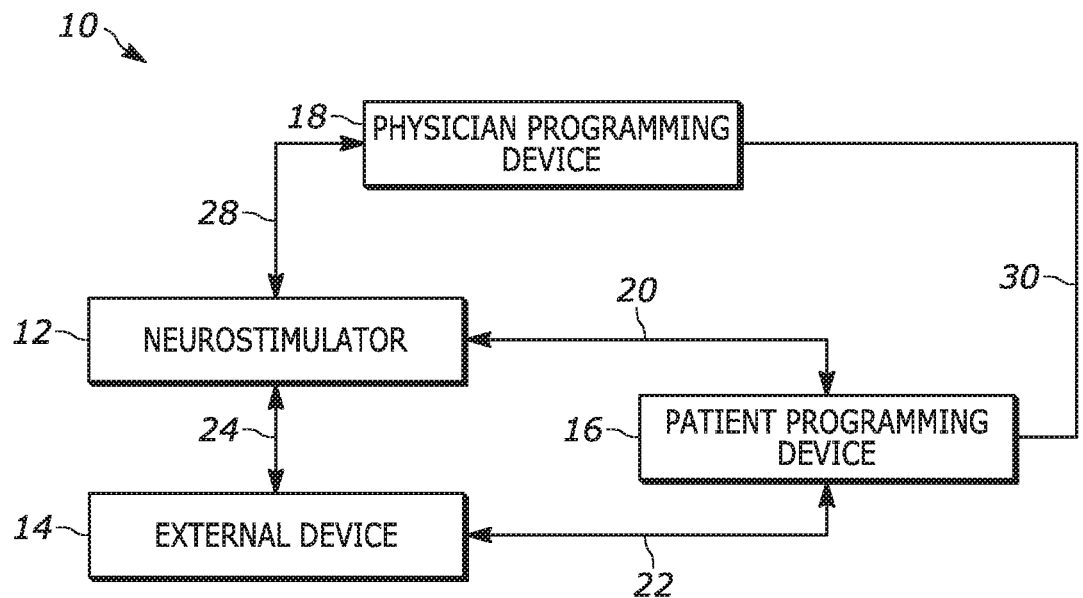
FIG. 5 is block diagram depicting illustrative components of a neuromodulation system according to an aspect of the present disclosure.
Figure 6:
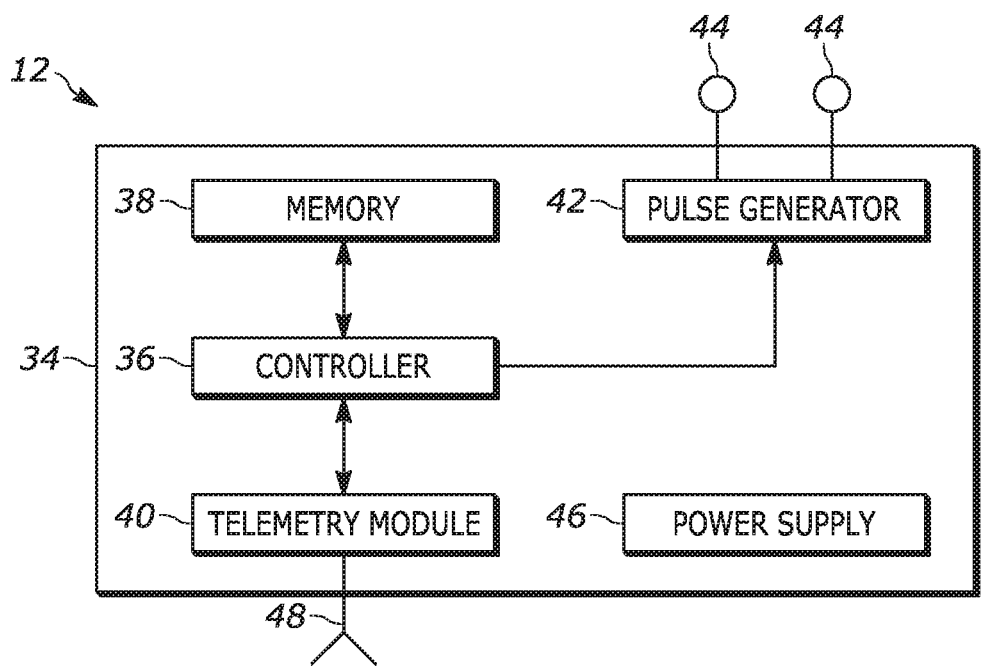
FIG. 6 is a block diagram depicting illustrative components of a neuromodulator according to an aspect of the present disclosure.

Aspects of the present disclosure also provide systems for improving SDB in a patient suffering therefrom. With reference to FIGS. 5 and 6, in an embodiment, a neurostimulation system 10 includes a neurostimulator 12, an external device 14 that transmits signals to neurostimulator 12, a patient programming device 16 that bi-directionally communicates with neurostimulator 12 and/or an external device 14, and a physician programming device 18. As discussed below, each component of a system can be in communication (e.g., electrical communication) with one another. In some instances, two or more components of a system can be in wireless communication with one another. In other instances, two or more components of a system can be in wired communication with one another. As such, some components of a system can be in wireless communication with one another while other components are in wired communication with one another. Further, in the illustrative embodiments disclosed herein, communication between components included in neurostimulation system 10 is configured to be bidirectional in nature. However, communication between two or more system components can be unidirectional. Further, the functionality of different components of the system can be combined into a single device. For example, the functionality of components of the external device and the patient programming device can be combined into a single device.

In an embodiment, neurostimulator 12 includes electronic circuitry, such as one or more electronic circuits, for delivering neurostimulation pulses enclosed in a sealed housing and coupled to electrodes. In certain embodiments, neurostimulator 12 can include a primary battery cell, a rechargeable battery cell, or an inductively coupled power source for providing power for generating and delivering stimulation pulses and powering other device functions such as communication functions. Neurostimulator 12 or system 10 can include fixation members to secure the neurostimulator to tissue adjacent to the target site.

External device 14 can be a wearable device including a strap, patch or another attachment member(s) for securing external device 14 to the patient in operable proximity to neurostimulator 12. In some instances, external device 14 can be programmed to provide user feedback to assist the patient in optimizing placement of external device 14 about the subject's body. When neurostimulator 12 is provided with a rechargeable battery cell, external device 14 can include a recharging unit for transmitting power, for example inductive power transmission, from external device 14 to neurostimulator 12. In this embodiment, programming device 16 can be a patient handheld device that is used to initiate and terminate therapy delivered by neurostimulator 12 via a bidirectional wireless telemetry link 20. Alternatively, programming device 16 can be operated by a patient for communicating with wearable external device 14 to control therapy on and off times and other therapy control parameters, which are transmitted to neurostimulator 12 via communication link 24. Programming device 16 can communicate with wearable external device 14 via a bidirectional wireless telemetry link 22 that can establish communication over a distance of up to a few feet, enabling distance telemetry such that the patient need not position programming device 16 directly over neurostimulator 12 to control therapy on and off times or perform other interrogation or programming operations (e.g., programming of other therapy control parameters).

When neurostimulator 12 includes primary cell(s), external device 14 can be optional. Programming of neurostimulator 12 can be performed by programming device 16, using near- or distance-telemetry technology for establishing a bidirectional communication link 20 for transmitting data between programming device 16 and neurostimulator 12. Programming device 16 can be used by a patient or clinician to set a therapy protocol that is performed automatically by neurostimulator 12. Programming device 16 can be used to manually start and stop therapy, adjust therapy delivery parameters, and collect data from neurostimulator 12, e.g. data relating to total accumulated therapy delivery time or other data relating to device operation or measurements taken by neurostimulator 12. For example, programming device 16 can include software programmed to control one or more stimulation and/or control parameters associated with neurostimulator 12. Additionally, or optionally, the software comprising programming device 16 can be programmed to store patient therapy data, such as diary questions or physiologic measurements. Programming device 16 can also include software programmed to access remote data sources, query certain data, and then provide stimulation instructions to system 10 based on the queried data. For example, programming device 16 can include software programmed to provide neurostimulator 12 with customizable or patient-triggered alerts, e.g., indicating stimulation periods and the duration of each period, after a desired period of time (e.g., 30 minutes) after sleep onset. Programming device 16 can be embodied as a smart phone or tablet, although personal computers (PCs) may also be included.

When neurostimulator 12 is configured as an externally powered device, external device 14 can be a power transmission device that is worn by the patient during sleep to provide power needed to generate stimulation pulses. For example, external device 14 can be a battery-powered device including a primary coil used to inductively transmit power to a secondary coil included in neurostimulator 12. External device 14 can include one or more primary and/or rechargeable cells and therefore can include a power adaptor and plug for re-charging in a standard 110V or 220V wall outlet, for example.

In some embodiments, the functionality required for transmitting power to neurostimulator 12 when neurostimulator 12 is embodied as a rechargeable or externally powered device and for programming the neurostimulator 12 for controlling therapy delivery can be implemented in a single external device. For example, power transmission capability of external device 14 and programming capabilities of patient programmer 16 can be combined in a single external device, which can be a wearable or handheld device (such as, for example, a smart phone or tablet).

Physician programming device 18 can include increased programming and diagnostic functionality compared to patient programming device 16. For example, physician programming device 18 can be configured for programming all neurostimulation therapy control parameters, such as, but not limited to, pulse amplitude, pulse width, pulse shape, pulse frequency, duty cycle, therapy on and off times, electrode selection, and electrode polarity assignments. Patient programming device 16 can be limited to turning therapy on and/or off, adjusting a start time of therapy, and/or adjusting a pulse amplitude without giving the patient full access to full programming functions such that some programming functions and programmable therapy control parameters cannot be accessed or altered by a patient.

Physician programming device 18 can be configured to communicate directly with neurostimulator 12 via wireless, bidirectional telemetry link 28 for example during an office visit. Additionally or alternatively, physician programming device 18 can be operable as a remote programming instrument used to transmit programming commands to patient programming device 16 via a wired or wireless communication network link 30, after which patient programming device 16 automatically transmits programming data to neurostimulator 12 via bidirectional telemetry link 20 (or via wearable external device 14 and link 24). Physician programming device can be embodied as a smart phone, tablet or PC, for example.

In some embodiments, the patient can be provided with a magnet for adjusting operation of neurostimulator 12. For example, application of the magnet can turn therapy on or off or cause other binary or stepwise adjustments to neurostimulator 12 operations.

FIG. 6 is a functional block diagram of neurostimulator 12 of FIG. 5 according to an embodiment of a neurostimulation system. Neurostimulator 12 can include a housing 34 enclosing a controller 36 and associated memory 38, a telemetry module 40, and a pulse generator 42 coupled to electrode(s) 44. Neurostimulator 12 includes a power supply 46, which as described above can include any of a primary battery cell, a rechargeable battery cell, and/or a secondary coil of an externally powered system.

Controller 36 can include any one or more of a microprocessor, a digital signal processor (DSP), an application specific integrated circuit (ASIC), a field-programmable gate array (FPGA), or equivalent discrete or integrated logic circuitry. In some examples, controller 36 can include multiple components, such as any combination of one or more microprocessors, one or more controllers, one or more DSPs, one or more ASICs, or one or more FPGAs, as well as other discrete or integrated logic circuitry. The functions attributed to controller 36 herein can be embodied as software, firmware, hardware or any combination thereof. In one example, a neurostimulation therapy protocol to improve an SDB in a patient can be stored or encoded as instructions in memory 38 that are executed by controller 36 to cause pulse generator 42 to deliver the therapy via electrodes 44 according to the programmed protocol.

Memory 38 can include computer-readable instructions that, when executed by controller 36, cause neurostimulator 12 to perform various functions attributed throughout this disclosure to the neurostimulator. The computer-readable instructions can be encoded within memory 38. Memory 38 can comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

Telemetry module 40 and associated antenna 48 can be provided for establishing bidirectional communication with external device 14, patient programmer 16 and/or physician programmer 18. Examples of communication techniques used by neurostimulator 12 and programming device 16 or 18 include low frequency or radiofrequency (RF) telemetry, which can be an RF link established via Bluetooth, WiFi, or MICS, for example. Antenna 48 can be located within, along or extend externally from housing 34.

Electrodes 44 can be located along an exterior surface of housing 44 and can be coupled to pulse generator 42 via insulated feedthroughs or other connections as will be further described below. In other embodiments, electrodes 44 can be carried by a lead or insulated tether electrically coupled to pulse generator 42 via appropriate insulated feedthroughs or other electrical connections crossing sealed housing 34. In still other embodiments, electrodes 44 can be incorporated in housing 34 with externally exposed surfaces adapted to be operably positioned in proximity to a target site proximate to a nerve and electrically coupled to pulse generator 42.

In another aspect, system 10 can include one or more sensors (not shown) to permit open- or closed-loop control. In an open-loop system, for example, system 10 can include one or more sensors such that a patient can manage (e.g., prophylactically) improvement of the SDB based on feedback (e.g., detected signals) from the sensor(s). Such detected signals can be indicative of the onset of the SDB, such as changes in muscle or nerve electrical activity, tongue position, oropharyngeal airflow, etc. Upon noticing the signal(s), the patient can then trigger or activate the neurostimulator 12 to prevent or mitigate the SDB.

In another aspect, system 10 can include one or more sensors to permit closed-loop control by, for example, automatically responding (e.g., by activation of the neurostimulator 12) in response to a sensed physiological parameter, or a related symptom or sign, indicative of the extent and/or presence of the SDB including respiratory state (e.g. inspiration/expiration) or changes in the sleep/wake state and or sleep stage (e.g. REM or non-REM), and/or onset/termination of sleep of the patient. Physiological parameters include changes in muscle or nerve electrical activity, tongue position, changes in heart rate or blood pressure, pressure changes in response to respiratory effort, oropharyngeal airflow, accelerometry data, positional data, electroencephalography data, etc. Sensors used as part of a closed- or open-loop system can be placed at any appropriate anatomical location on a patient, including a skin surface, an oral cavity, a nasal cavity, a mucosal surface, or at a subcutaneous location. Sensors can also be placed proximate but not in contact with the patient, such as a sensor placed in proximity to the patient that detects respiratory effort which then communicates with the neurostimulator by wired or wireless fashion. In certain aspects, a system can include sensors to detect an SDB event and activate or pace respiration or adjust a duty cycle after automatic detection of the patient's sleep state.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance. Further, while the above is described with respect to electrical stimulation, other forms of electromagnetic energy could be used, such as, for example, ultrasound, magnetic, radiofrequency, thermal, or optical energy.

What is claimed is:

1. A therapy delivery system for improving sleep disordered breathing comprising:
   at least one implantable electrode;
   and
   a controller in electrical communication with the at least one implantable electrode and programmed to direct delivery of at least one electrical signal proximate an ansa cervicalis to stimulate the ansa cervicalis and activate a sternothyroid muscle to improve the sleep disordered breathing.

2. The therapy delivery system of claim 1, further comprising:
   the controller further being programmed to direct delivery of the at least one electrical signal proximate to the ansa cervicalis to stimulate the ansa cervicalis and activate a sternohyoid muscle.

3. The therapy delivery system of claim 2, further comprising:
   the controller further being programmed to direct delivery of the at least one electrical signal proximate to the ansa cervicalis to stimulate the ansa cervicalis and activate an omohyoid muscle.

4. The therapy delivery system of claim 1, further comprising:
   the controller programmed to direct delivery of the at least one electrical signal proximate to the ansa cervicalis to stimulate the ansa cervicalis and activate an omohyoid muscle.

5. The therapy delivery system of claim 1, further comprising:
   the controller further being programmed to direct delivery of the at least one electrical signal to a hypoglossal nerve to activate a genioglossus muscle.

6. The therapy delivery system of claim 1, wherein the at least one implantable electrode is a plurality of implantable electrodes.

7. The therapy delivery system of claim 1, further comprising a sensor configured to sense a physiological parameter indicative of a presence, onset or extent of the sleep disordered breathing.

8. The system of claim 7, wherein the controller is programmed to activate the at least one implantable electrode in response to the sensed physiological parameter to improve the sleep disordered breathing.

9. The system of claim 7, wherein the sensor is configured to detect a sleep disordered breathing event and the controller is programmed to activate the at least one implantable electrode to activate or pace respiration after detection of the sleep disordered breathing event.

10. The system of claim 7, wherein the sensor is configured to detect a patient's sleep state and the controller is programmed to adjust a duty cycle of the electrical signal after automatic detection of the patient's sleep state.

11. A method of improving sleep disordered breathing in a patient suffering therefrom comprising:
  obtaining the system of claim 1;
  delivering the at least one electrical signal proximate to the ansa cervicalis to stimulate the ansa cervicalis innervating the sternothyroid muscle;
  activating the sternothyroid muscle; and
  improving the patient's sleep disordered breathing via delivery of the at least one electrical signal.

12. The method of claim 11, further comprising:
  delivering the at least one electrical signal proximate to the ansa cervicalis to stimulate the ansa cervicalis innervating a sternohyoid muscle; and
  activating the sternohyoid muscle.

13. The method of claim 12, further comprising:
  delivering the at least one electrical signal proximate to a hypoglossal nerve innervating a genioglossus muscle; and
  activating the genioglossus muscle.

14. The method of claim 13, wherein proximate to the hypoglossal nerve comprises distal to or at a branch point of the hypoglossal nerve and a superior root of the ansa cervicalis.

15. The method of claim 13, wherein proximate to the hypoglossal nerve comprises distal to a branch point of the hypoglossal nerve innervating tongue retractor muscles.

16. The method of claim 11, wherein proximate to the ansa cervicalis comprises proximal to or at a branch point of a superior root of the ansa cervicalis.

17. The method of claim 11, wherein proximate to the ansa cervicalis comprises proximate to an inferior root of the ansa cervicalis.

18. The method of claim 11, further comprising:
  delivering the at least one electrical signal proximate to the ansa cervicalis to stimulate the ansa cervicalis innervating an omohyoid muscle; and
  activating the omohyoid muscle.

19. The method of claim 11, further comprising:
  delivering the at least one electrical signal proximate to a hypoglossal nerve innervating a genioglossus muscle; and
  activating the genioglossus muscle.

20. The method of claim 11, wherein the sleep disordered breathing is obstructive sleep apnea.

* * * * *